United States Patent [19]

Cameron et al.

[11] Patent Number: 5,627,186

[45] Date of Patent: May 6, 1997

[54] ANTIVIRAL COMBINATIONS

[75] Inventors: Janet M. Cameron; Nicholas Cammack, both of Greenford, Great Britain

[73] Assignee: Glaxo Group Limited, Great Britain

[21] Appl. No.: 219,176

[22] Filed: Mar. 28, 1994

Related U.S. Application Data

[63] Continuation of Ser. No. 883,169, May 15, 1992, abandoned.

[30] Foreign Application Priority Data

| May 16, 1991 | [GB] | United Kingdom | 9110624 |
| Oct. 8, 1991 | [GB] | United Kingdom | 9121381 |
| Nov. 6, 1991 | [GB] | United Kingdom | 9123581 |

[51] Int. Cl.⁶ ........................ A61K 31/70; A61K 31/505
[52] U.S. Cl. .................................. 514/274; 514/50
[58] Field of Search ................................ 514/50, 274

[56] References Cited

U.S. PATENT DOCUMENTS 5,047,407  9/1991  Belleau et al. ................ 514/274
5,116,823  5/1992  Calabresi et al. ................ 514/50

OTHER PUBLICATIONS

Spector et al, Antimicrobial Agent & Chemotherapy vol. 33, pp. 920–923 1989.

*Primary Examiner*—Russell Travers
*Attorney, Agent, or Firm*—Bacon & Thomas

[57] ABSTRACT

Combinations comprising a compound of formula (1)

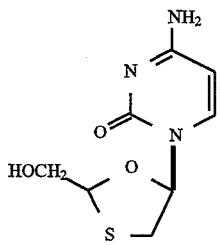

or a pharmaceutically acceptable derivative thereof and an inhibitor of HIV replication, pharmaceutical formulations thereof and their use in the treatment of HIV infections.

6 Claims, 4 Drawing Sheets

3TC/TIBO ISOBOLOGRAM

3TC 150% 0.34 : TIBO 150% 0.008

- ● COMPOUND OF EXAMPLE 1, CELL CONTROL VALUE = 19816 cpm
- ◇ AZT, CELL CONTROL VALUE = 13328 cpm
- ▽ COMBINATION (1:1), CELL CONTROL VALUE = 13328 cpm

ANTIVIRAL COMBINATIONS

This application is a continuation of application Ser. No. 07/833,169, now abandoned, filed May 15, 1992.

The present invention relates to combinations of antiviral agents. More specifically it is concerned with combinations of 1,3-oxathiolane nucleoside analogues with other antiviral agents, in particular agents effective against HIV.

Human immunodeficiency virus (HIV) causes a variety of clinical conditions including the acquired immune deficiency syndrome (AIDS) and chronic neurological disorders. Nucleosides such as AZT, ddC and ddI inhibit HIV replication in vitro, and appear to exert their antiviral activity on the virus-encoded reverse transcriptase enzyme after metabolism by the cell to their 5'-triphosphate derivatives.

AZT reduces morbidity and mortality in patients with AIDS. However, HIV infection of cells results in integration of the virus genome into the host chromosome, and so it has been necessary to continue AZT treatment for long periods of time. The consequences of long-term AZT therapy are associated bone-marrow toxicity and the appearance of AZT-resistant variants of HIV-1. Similarly, some AIDS patients treated with ddC develop peripheral neurophathy and ddI has been shown to induce pancreatitis and peripheral neuropathy.

The use of combinations of compounds may give rise to an equivalent antiviral effect with reduced toxicity, or an increase in drug efficacy if synergy between compounds occurs. Lower overall drug doses will possibly also reduce the frequency of occurrence of drug-resistant variants of HIV. Many different methods have been used to examine the effects of combinations of compounds acting together in different assay systems. All of these methods have limitations and for example, some methods have been applied to systems other than those for which they were derived. AZT demonstrates synergistic antiviral activity in vitro in combination with agents that act at HIV-1 replicative steps other than reverse transcription, including recombinant soluble CD4 castanospermine and recombinant interferon alpha. However, it must be noted that combinations of compounds can give rise to increased cytotoxicity. AZT and recombinant interferon alpha have an increased cytotoxic effect on normal human bone marrow progenitor cells.

Combinations of AZT with other nucleosides have also been investigated. ddC eliminates the bone marrow cytotoxicity of high-dose AZT without affecting its antiviral activity. ddt and AZT show some enhanced selectivity in combination, through a synergistic antiviral effect acting over an additive toxicity to normal human bone marrow progenitor cells.

The compound of formula (I)

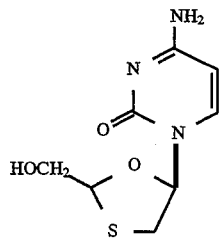

also known as BCH-189 or NGPB-21 has been described as having antiviral activity in particular against the human immunodeficiency viruses (HIV's), the causative agents of AIDS (5th Anti-Aids Conference, Montreal, Canada 5th–9th June 1989: Abstracts T.C.O.1 and M.C.P. 63; European Patent Application Publication No. 0382562). The compound of formula (I) is a racemic mixture of the two enantiomers of formulae (I-1) and (I-2):

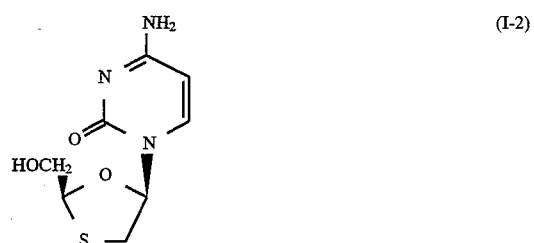

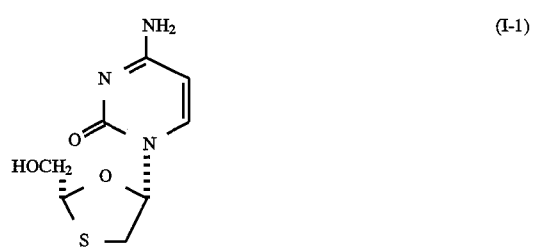

Although the enantiomers of the compound of formula (I) are equipotent against HIV one of the enantiomers (the (−)-enantiomer) has considerably lower cytotoxicity than the (+) enantiomer.

The (−) enantiomer has the chemical name (−)cis-4-Amino-1-(2-hydroxymethyl-1,3-oxathiolan-5-yl)-(1H)-pyrimidin-2-one. It has the absolute stereochemistry of the compound of formula (I-1) which has the name (2R,cis))-4-amino-1-(2-hydroxymethyl-1,3-oxathiolan-5-yl)-(1H)-pyrimidin-2-one. This compound is now known as 3TC.

We have now found that the compound of formula (I) and, in particular its (−)-enantiomer exhibits unexpected advantages when used in combination with known inhibitors of HIV replication. In particular the compound of formula (I) shows a synergistic antiviral effect and/or a reduction in cytotoxicity when used in combination with known inhibitors of HIV replication.

There is thus provided in a first aspect of the invention a combination comprising the compound of formula (I) or a pharmaceutically acceptable derivative thereof and an inhibitor of HIV replication.

The inhibitor may comprise any inhibitor of HIV replication no matter its method of inhibiting HIV replication.. Such inhibitors include for example those which inhibit HIV reverse transcriptase, HIV protease and TAT and the like.

Such inhibitors include for example 3'-azido-3'-deoxythymidine (AZT, zidovudine), 2',3'-dideoxycytidine (ddC), 2',3'-dideoxyinosine (ddI), N'-[1-(S)-benzyl-3-[4a(S),8a(S)-3(S)-(tert-butylcarbamoyl) decahydroisoquinoline-2-yl]-2(R)-hydroxypropyl]-N"-(quinolin-2-ylcarbonyl)-L-asparaginamide (Ro 31-8959) and (+)-S-4,5,6,7-tetrahydro-5-methyl-6-(3-methyl-2-butenyl)-imidazo(4,5,1-jk)(1,4)-benzodiazepin-2(1H)thione (R-82150; TIBO) or a pharmaceutically acceptable derivative thereof.

Preferably the compound of formula (I) is in the form of its (−) enantiomer (3TC). Preferably the inhibitor of HIV replication is selected from AZT, ddI, Ro 31-8959 or R-82150(TIBO).

Particularly preferred as the inhibitor of HIV replication is ddI or, especially, AZT.

When the Compound formula (I) is in the form of the (−)-enantiomer it will normally be provided substantially free of the corresponding (+)-enantiomer, that is to say no more than about 5% w/w of the (+)-enantiomer, preferably no more than about 2%, in particular less than about 1% w/w will be present. By "a pharmaceutically acceptable derivative" is meant any pharmaceutically acceptable salt, ester, or salt of such ester, of a parent compound or any other compound which, upon administration to the recipient, is capable of providing (directly or indirectly) the parent compound or an antivirally active metabolite or residue thereof.

It will be appreciated by those skilled in the art that the compound of formula (I) may be modified to provide pharmaceutically acceptable derivatives thereof, at functional groups in both the base moiety and at the hydroxymethyl group of the oxathiolane ring. Modification at all such functional groups are included within the scope of the invention. However of particular interest are pharmaceutically acceptable derivatives obtained by modification of the 2-hydroxymethyl group of the oxathiolane ring.

Preferred esters of the compound of formula (I) include the compounds in which the hydrogen of the 2-hydroxymethyl group is replaced by an acyl function

in which the non-carbonyl moiety R of the ester is selected from hydrogen, straight or branched chain alkyl (e.g. methyl, ethyl, n-propyl, t-butyl, n-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); amino acid esters (e.g. L-valyl or L-isoleucyl) and mono-, di- or tri-phosphate esters.

With regard to the above described esters, unless otherwise specified, any alkyl moiety present advantageously contains 1 to 16 carbon atoms, particularly 1 to 4 carbon atoms. Any aryl moiety present in such esters advantageously comprises a phenyl group.

In particular the esters may be a $C_{1-6}$alkyl ester, an unsubstituted benzyl ester or a benzyl ester substituted by at least one halogen (bromine, chlorine, fluorine or iodine), $C_{1-6}$alkyl, $C_{1-6}$alkoxy, nitro or trifluoromethyl groups.

Pharmaceutically acceptable salts of the compound of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4+$ (where R is $C_{1-4}$alkyl) salts.

The compound of formula (I) is either synergistic with the second component of the combination and/or removes the cytotoxic effects of the second component.

The advantageous effects of the compounds of formula (I) and the second antiviral agents are realised over a wide ratio for example 1:250 to 250:1 preferably 1:50 to 50:1, particularly about 1:10 to 10:1. Conveniently each compound will be employed in the combination in an amount at which it exhibits antiviral activity when used alone.

It is expected that the present combinations will be generally useful against vital infections or virus-associated tumours in humans, and the method of their use to inhibit viral infectivity or tumour growth in vitro or in vivo is also within the scope of the present invention.

Thus there is provided in a second aspect a method for the treatment of a viral infection in a mammal, including man, comprising co-administration of an antiviral compound of formula (I) and an inhibitor of HIV replication. Therapeutic methods comprising administration of a combination of a compound of formula (I) and more than one of the second antiviral agents, either together or in a plurality of paired combinations, is also within the scope of the invention.

It will be appreciated that the compound of formula (I) and the second antiviral agent may be administered either simultaneously, sequentially or in combination. If administration is sequential, the delay in administering the second of the active ingredients should not be such as to lose the benefit of the synergistic effect of the combination. Preferably administration will be simultaneous.

It will be appreciated by those skilled in the art that reference herein to treatment extends to prophylaxis as well as the treatment of established infections or symptoms.

It will be further appreciated that the amount of a combination of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 1 to about 750 mg/kg e.g. from about 10 to about 75-mg/kg of bodyweight per day, such as 3 to about 120 mg per kilogram body weight of the recipient per day, preferably in the range of 6 to 90 mg/kg/day, most preferably in the range of 15 to 60 mg/kg/day of each of the active ingredients of the combination.

The desired dose may conveniently be presented in a single dose or as divided doses administered at appropriate intervals, for example as two, three, four or more sub-doses per day.

The combination is conveniently administered in unit dosage form; for example containing 10 to 1500 mg, conveniently 20 to 1000 mg, most conveniently 50 to 700 mg of each active ingredient per unit dosage form.

Ideally the combinations should be administered to achieve peak plasma concentrations of each of the active compound of form about 1 to about 75 mM, preferably about 2 to 50 mM, most preferably about 3 to about 30 mM. This may be achieved, for example, by the intravenous injection of a 0.1 to 5% solution of the active ingredients, optionally in saline, or orally administered as a bolus containing about 1 to about 100 mg of each active ingredient. Desirable blood levels may be maintained by a continuous infusion to provide about 0.01 to about 5.0 mg/kg/hour or by intermittent infusions containing about 0.4 to about 15 mg/kg of each active ingredient.

While it is possible that, for use in therapy, the active ingredients of the combination may be administered as the raw chemical it is preferable to present combinations as a pharmaceutical formulation.

The invention thus further provides a pharmaceutical formulation comprising a compound of formula (I) or a pharmaceutically acceptable derivative thereof and inhibitor of HIV replication together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one more dispersing agents, solubilising agents or suspending agents. Liquid sprays are conveniently delivered from pressurised packs.

For administration by inhalation the compounds according to the invention are conveniently delivered from an insufflator, nebuliser or a pressurised pack or other convenient means of delivering an aerosol spray. Pressurised packs may comprise a suitable propellant such as dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compound of formula (I) may be obtained as described in European Patent Application Publication No. 0382562.

Its individual enantiomers may be obtained from its racemate by resolution by any method known in the art for the separation of racemates into their constituent enantiomers. In particular they may be obtained from the known racemate by chiral HPLC, by enzyme mediated enantioselective catabolism with a suitable enzyme such as cytidine deaminase or by selective enzymatic degradation of a suitable derivative using a 5'-nucleotide. Methods for the preparation of 3TC are described in International Patent Application Publication No. WO91/17 159.

Figure 1:
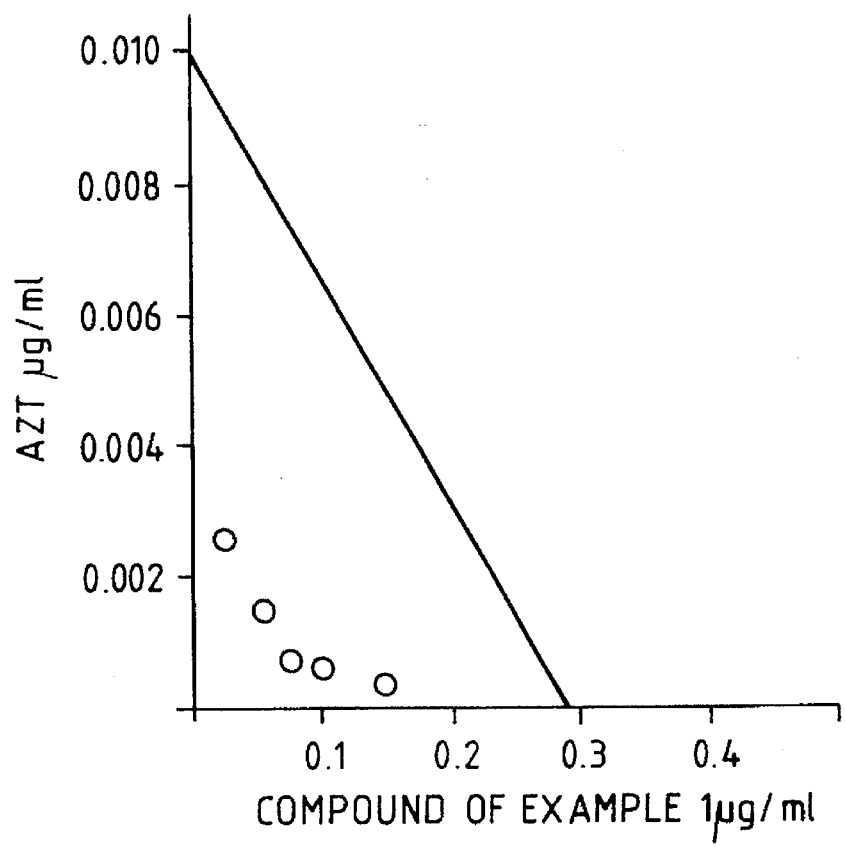
FIG. 1 shows a dose response curve for 3TC in combination with AZT.
Figure 2:
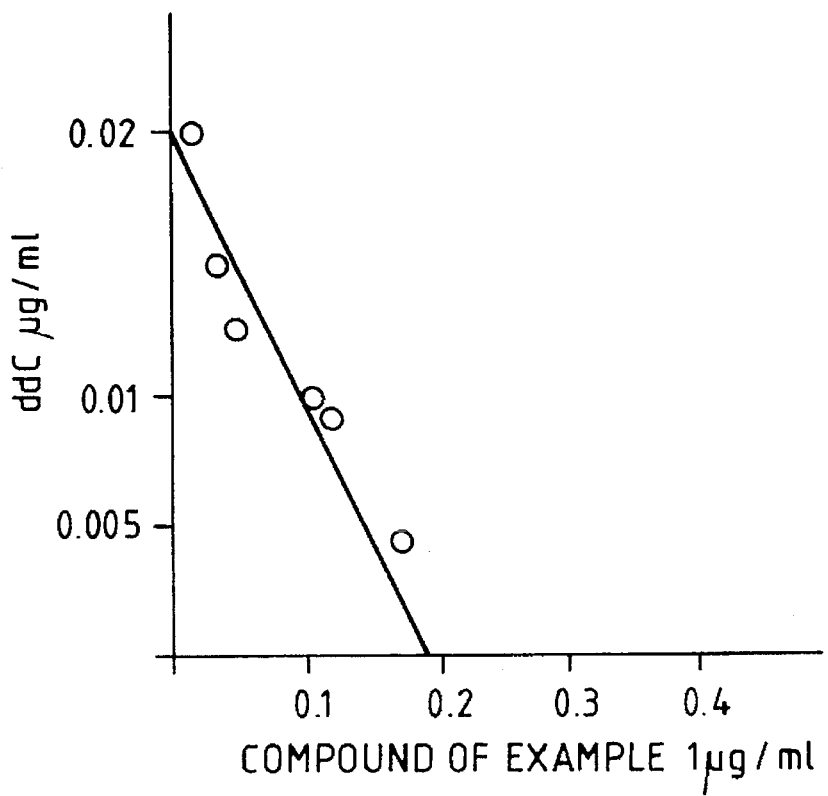
FIG. 2 shows a dose response curve for 3TC in combination with ddC.
Figure 3:
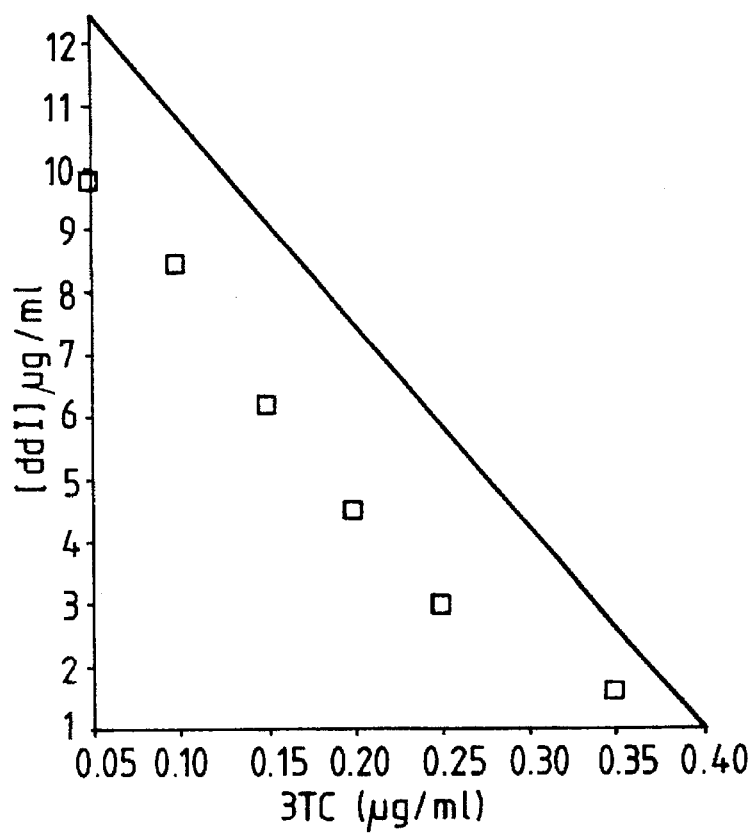
FIG. 3 shows a dose response curve for 3TC in combination with ddI.
Figure 4:
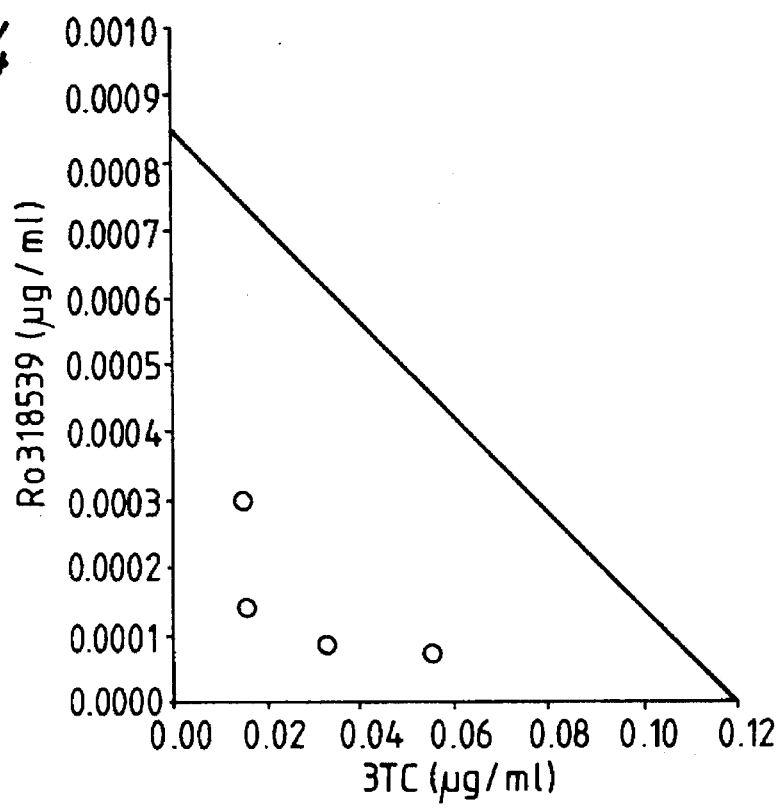
FIG. 4 shows a dose response curve for 3TC in combination with Ro 31-8959.
Figure 5:
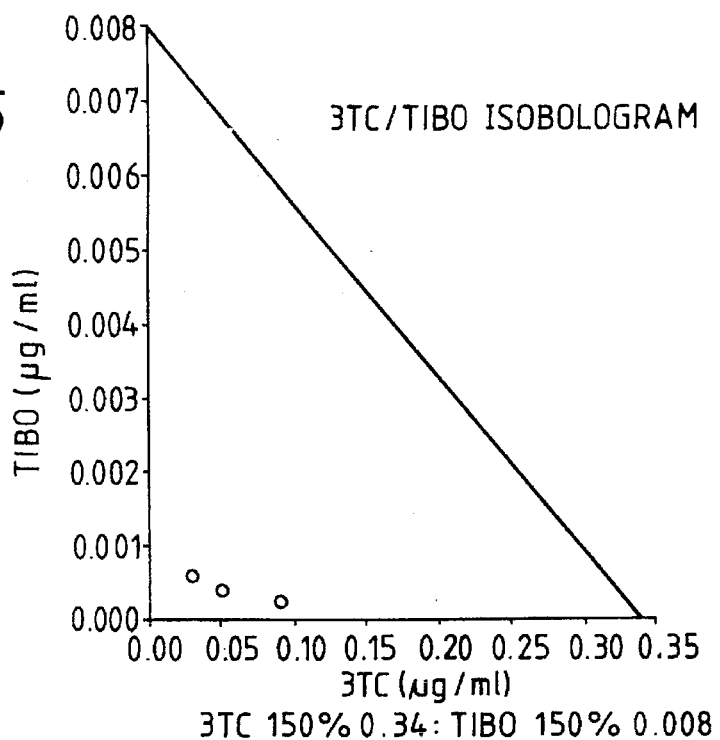
FIG. 5 shows a dose response curve for 3TC in combination with R-82150 (TIBO).

The following examples illustrate the invention but are not intended as a limitation thereof.

INTERMEDIATE 1

5-Methoxy-1,3-oxathiolane-2-methanol, benzoate.

A solution of zinc chloride (1.6 g) in hot methanol (15 ml) was added to a stirred solution of mercaptoacetaldehyde, dimethyl acetal (34.2 g) and benzoyloxy acetaldehyde (48.3 g) in toluene (1300 ml) which was then heated to reflux under nitrogen for 50 min. The cooled mixture was concentrated, diluted with some toluene, then filtered through Kieselguhr. The combined filtrates and toluene were washed with aqueous saturated sodium bicarbonate solution (×2) and brine, dried (MgSO$_4$) then evaporated to an oil which was subjected to column chromatography on silica (2 kg, Merck 9385) eluted with chloroform to give the title product as an oil (45.1 g) a mixture of anomers (ca 1:1); 1H NMR (DMSO-d$_6$) 3.1–3.3(4H), 3.42(6H), 4.4–4.6 (4H), 5.41(1H), 5.46 (1H), 5.54 (1H), 5.63 (1H), 7.46 (4H), 7.58 (2H), 8.07 (4H);γmax (CHBr$_3$)1717.6cm$^{-1}$.

INTERMEDIATE 2

(±)-cis-1-(2-Benzoyloxymethyl-1,3-oxathiolan-5-yl)-(1H)-pyrimidin-2-4-dione

A mixture of finely ground uracil (9.62 g) hexamethyl disilazane (50 ml) and ammonium sulphate (30 mg) was heated at reflux under nitrogen until a clear solution was obtained. This was cooled and then evaporated to a colourless oil, which was dissolved, under nitrogen atmosphere, in acetonitrile (100 ml). The solution was added to a stirred ice cooled solution of 5-methoxy-1,3-oxathiolane-2-methanol, benzoate (intermediate 1) (19.43 g), in acetonitrile (600 ml) and trimethyl silyl trifluoromethanesulphonate (14.7 ml) was added. The ice bath was removed, and the solution was heated at reflux under nitrogen for 45 mins. After cooling and evaporation, the residue was purified by column chromatography over 1 kg of silica gel (Merck 9385) eluting with chloroform/methanol 9:1. Appropriate fractions were cooled and evaporated to afford a crude residue. This was fractionally crystallized from the minimum of hot methanol (c. 1200 ml) to afford the title compound (6.32 g) as white crystals. 1H NMR(d$_6$DMSO) δ 11.36 (1H,bs), 7.50–8.00 (6H,m), 6.20 (1H,t), 5.46 (2H,m), 4.62 (2H, m), 3.48 (1H, m), 3.25 (1H, m).

INTERMEDIATE 3

(±)-(cis)-4-Amino-1-(2-benzoyloxymethyl-1,3-oxathiolan-5-yl)-(1H)-pyrimidin-2-one

Method (a)

A suspension of cytosine (20.705 g) and ammonium sulphate (few mgs) in hexamethyldisilazane (110 ml) was stirred and heated at reflux for 2½ h, under nitrogen. Solvent was removed by evaporation, and the residual solid was dissolved in dry acetonitrile (350 ml). This solution was transferred using flexible needle techniques into a stirred, ice-chilled solution of 5-methoxy-1,3-oxathiolane-2-methanol, benzoate (Intermediate I) (43.57 g) in acetonitrile (650 ml) under nitrogen. Trimethylsilyl trifluoromethanesulphonate (33 ml) was added, the solution was allowed to warm to ambient temperature (1½ h) then heated to reflux for an overnight period. The residue mixture was concentrated, diluted with saturated aqueous sodium bicarbonate solution (500 ml), then extracted with ethyl acetate (3×500 ml). The combined extracts were washed with water (2×250 ml) and brine (250 ml) dried (MgSO$_4$) then evaporated to a foam which was subjected to column chromatography on silica (600 g, merck 7734), eluted with ethyl acetate-methanol mixtures to give a mixture of anomers (ca 1:1 31.59 g). The mixture was crystallised from water (45 ml) and ethanol (9.0 ml) to give a solid (10.23 g) which was recrystallised from ethanol (120 ml) and water (30 ml) to give the title product as a white solid (9.26 g); γmax (MeOH) 229.4 mm (E$^{1\%}$ 610); 272.4mm (E$^{1\%}$ 293); $^1$H NMR (DMSO d$_6$) δ 3.14 (1H), 3.50 (1H), 4.07 (2H), 5.52 (1H), 5.66 (1H), 6.28 (1H), 7.22 (2H), 7.56 (2H), 7.72 (2H), 8.10 (2H).

Method (b)

Phosphorus oxychloride (7.0 ml) was added dropwise to a stirred, ice-cooled suspension of 1,2,4-triazole (11.65 g) in acetonitrile (120 ml) then, keeping the internal temperature below 15° C., triethylamine (22.7 ml) was added dropwise. After 10 min a solution of (±)-cis -1-(2-benzoyloxymethyl-1,3-oxathiolan-5-yl)-(1H)-pyrimidin-2,4-dione (Intermediate 2) (6.27 g) in acetonitrile (330 ml) was slowly added. Stirring was then continued at room temperature overnight. The mixture was cooled by means of an ice bath and triethylamine (30 ml) was slowly added followed by water (21 ml). The resultant solution was evaporated, and the residue was partitioned between saturated sodium bicarbonate solution (400 ml) and chloroform (3×200 ml). The combined chloroform extracts were dried and magnesium sulphate, filtered and evaporated to give a crude residue (9.7 g). The residue was dissolved in 1,4-dioxan (240 ml) and concentrated aqueous ammonia solution (e.g 0.880, 50 ml) was added. After 1½ h the solution was evaporated and the residue dissolved in methanol. This caused precipitation of a solid, which was filtered off. The mother liquors were purified by column chromatography over silica gel (Merck 9385, 600 g). Appropriate fractions were pooled and evaporated to give the title compound as a fawn solid (2.18 g), identical to that obtained by Method (a).

INTERMEDIATE 4

(±)-(cis)-4-Amino-1-(2-hydroxymethyl-1,3-oxathiolan-5-yl)-(1H)-pyrimidin-2-one A suspension of (cis)-4-amino-1-(2-benzoyloxymethyl-1,3-oxathiolan-5-yl)(1H)-pyrimidin-2-one (Intermediate 3) (8.19 g) and Amberlite IRA-400 (OH) resin (8.24 g) in methanol (250 ml) was stirred and heated to reflux for 1¼ h. Solids were removed by filtration then washed with methanol. The combined filtrates were evaporated. The residue was triturated with ethyl acetate (80 ml). The resulting white solid was collected by filtration to give the title product (5.09 g). 1H NMR (DMSO-d$_6$) 3.04 (1H), 3.40 (1H), 3.73 (2H), 5.18 (1H), 5.29 (1H), 5.73 (1H), 6.21 (1H), 7.19 (2H), 7.81 (1H).

EXAMPLE 1

(−)-cis-4-Amino-1-(2-hydroxymethyl-1,3-oxathiolan-5-yl)-(1H) pyrimidin-2-one (i) Three 50 ml flasks of nutrient broth (Oxoid Ltd) were inoculated with a loopful each of *Escherichia coli* (ATCC 23848) scraped from a Nutrient Agar plate. The flasks were incubated overnight at 37° C. with shaking at 250 rev/min and then each flask was used to innoculate 4l of CDD medium (glutamic acid, 3 g/l; MgSO$_4$, 0.2 g/l: K$_2$SO$_4$, 2.5 g/l; NaCl, 2.3 g/l, Na$_2$HPO$_4$2H$_2$O, 1.1 g/l, NaH$_2$PO$_4$2H$_2$O 0.6 g/l cytidine, 1.2 g/l) in a seven liter fermenter. The cultures were fermented at 750 rev/min, 37° C. with aeration at 4l/min. After growth for 24 hrs the cells were collected by centrifugation (5000 g, 30 minutes) to yield 72 g wet weight. The cell pellet was resuspended in 300 ml of 20 mM Tris HCl buffer (pH 7.5) and disrupted by sonication (4×45 seconds). The cell debris was removed by centrifugation (30,000 g, 30 minutes) and the protein in the supernatant was precipitated by addition of ammonium sulphate to 75% saturation. The precipitate was collected by centrifugation (30,000 g. 30 minutes) and the pellet was resuspended in 25 ml of HEPES buffer (100 mM, pH 7.0) containing ammonium sulphate (75% saturation). Enzyme solution was prepared by centrifugation at 12,000 rpm for 30 mins. The supernatant was discarded and the pellet dissolved in Tris HCl buffer (pH 7.0; 100 mM) to the original volume.

(ii) Intermediate 4 (115 mg was dissolved in water (100 ml), and stirred. Enzyme solution (0.5 ml) was added, and the mixture was maintained at a constant pH by the continual addition of HCl (25mM). The conversion was monitored by chiral HPLC, which showed that the (+) enantiomer of the substrate was preferentially deaminated. After 22 hr the (+) enantiomer of the substrate (RT 12.5 min) had been completely removed, and the solution was adjusted to pH 10.5 by the addition of conc. sodium hydroxide.

The solution produced above was eluted through a column of QAE Sephadex (A25; Pharmacia; 30×1.6 cm), pre-equilibrated to pH11. The column was washed with water (200 ml) and then with HCl (0.1M). Fractions (40 ml) were taken, and analysed by reversed phase HPLC. Fractions 5–13, containing the unreacted (−) enantiomer of the substrate, were combined and adjusted to pH 7.5 with HCl. Fraction 47, containing deaminated product, was adjusted to pH 7.5 with dil. NaOH. Analysis by chiral HPLC showed that this material was a mixture, consisting of one enantiomer (RT 10.2 min) as the major component with the other enantiomer (RT 8.5 min) as a minor component (e.e ca 90%).

(iii) Stage (ii) above was repeated on a larger scale. The compound of Example 1 (363 mg) in 250 ml of water was incubated with enzyme solution (0.5 ml), prepared as in Stage (i). Further aliquots (0.5 ml) of enzyme were added after 18 and 47 hrs. The reaction mixture was stirred for 70 hr., then left standing for a further 64 hr. Analysis by chiral hplc indicated that the (+) enantiomer of the substrate had been completely deaminated, and the resulting solution was adjusted to pH10.5 with NaOH.

The solution above was loaded onto the same QAE column, and eluted as in stage (i). Fractions 2–6, containing a mixture of the residual substrate and deaminated product, were bulked. Fractions 7–13, containing the residual substrate ((−) enantiomer), were bulked and adjusted to pH7.5. Fractions 25–26, containing deaminated product, were bulked and neutralised Fractions 2–6 above were re-eluted through the same QAE column. Fractions 3–11 from this second column contained unrected substrate ((−) enantiomer). Fraction 70 contained the deaminated product.

(iv) The resolved substrate fractions from stage (ii) and (iii) were combined and adjusted to pH7.5. This solution was eluted through a column of XAD-16 (40×2.4cm), packed in water. The column was washed with water, and then eluted with acetone: water (1:4 v/v). Fractions containing the desired (−) enantiomer were bulked and freeze-dried to give a white powder (190 mg).

The HPLC methods used above were as follows:

1. Reversed Phase analytical HPLC

Column: Capital Cartridge Spherisorb ODS-2 (5 uM) 150×4.6 mm.

Eluant: Ammonium dihydrogen phosphate (50 mM)+5% MeCN.

Flow: 1.5 ml/min.

Detection: UV, 270 nm.

Retention Times: BCH 189 5.5 min deaminated BCH-189 8.1 min.

2. Chiral analytical HPLC

Column: Cyclobond I Acetyl 250×4.6 mm.

Eluant: 0.2% Triethylammonium acetate (pH7.2).

Flow: 1.0 ml/min.

Detection: UV, 270 nm.

Retention Times: BCH 189 11.0 and 12.5 min: deaminated BCH-189 8.5 and 10.2 min (The bioconversion was followed by monitoring the loss of the peak at 12.5 min., and accumulated of product at 10.2 min).

EXAMPLE 2

3.1 Antiviral Activities Alone or in Combination

Compounds were first serially-diluted in 2-fold decrements in 96-well microtitre plates. Chequerboard titrations were prepared by mixing 25 ml aliquots from each compound dilution both alone or in combination (to a final volume of 50 ml in new 96-well microtitre plates). Aliquots of MT-4 cells ($10^6$ cells/ml) in RPMI 1640 growth medium were infected with HIV-1 strain RF at a moi of $2\times10^{-3}$ infectious doses/cell. Virus was adsorbed at room temperature for 90 minutes, after which the cells were washed in RPMI 1640 growth medium to remove unadsorbed virus and resuspended at $10^6$ cells/ml in RPMI 1640 growth medium. 50 ml of infected cell suspension were inoculated into wells containing compound or growth medium only. 50 ml of mock-infected cell suspension were inoculated into wells not containing compound. The plates were then incubated for 7 days at 37° C. in 5% $CO_2$/air.

After incubation, 10 ml of 3-[4,5-dimethyl thiazol-2-yl]-2,5-diphenyltetrazolium bromide (MTT) at 7.5 mg/ml were added to all wells and the plates incubated for a further 90 minutes at 37° C. 150 ml of 10% (v/v) Triton X-100 in isopropanol were then added and the cells re, suspended. After 15 minutes at room temperature the plates were analysed in a Multiskan MC (Flow Laboratories, Irvine, UK) reader at 405 nm. Conversion of yellow MTT to its formazan derivative is maximum in the uninfected untreated cells, and absent in untreated infected cells. Dose-response curves were plotted for each compound alone (IC50% values) and for reciprocal titrations of each compound at a fixed concentration of the second compound. Isobolograms of all compound combinations giving IC50% values were plotted.

FIGS. 1 to 5 are isobolograms of 3TC in combination with AZT, ddC, ddI, Ro 31-8959 and R-82150(TIBO) respectively. If the IC50% values of compound combination lies on a line joining the IC50% values of each compound on its own, then the two compounds act additively. If the combination IC50% lie to the left of the line, the compounds are acting synergistically.

Dose response curve for 3TC in combination with AZT, ddC, ddI, Ro 31-8959 and R-82150 (TIBO) are shown in FIGS. 1–5, respectively.

No toxic effects were observed when the antiviral activities of the combinations were determined.

EXAMPLE 3

Cytotoxicities of Compounds Alone and in Combination

In these experiments the cytotoxicities of 3TC, AZT and ddC alone and in combination (at mg/ml ratios of 1:1, 1:5 and 5:1) were compared in uninfected peripheral blood lymphocytes and an established T-lymphocyte cell line.

Figure 6:
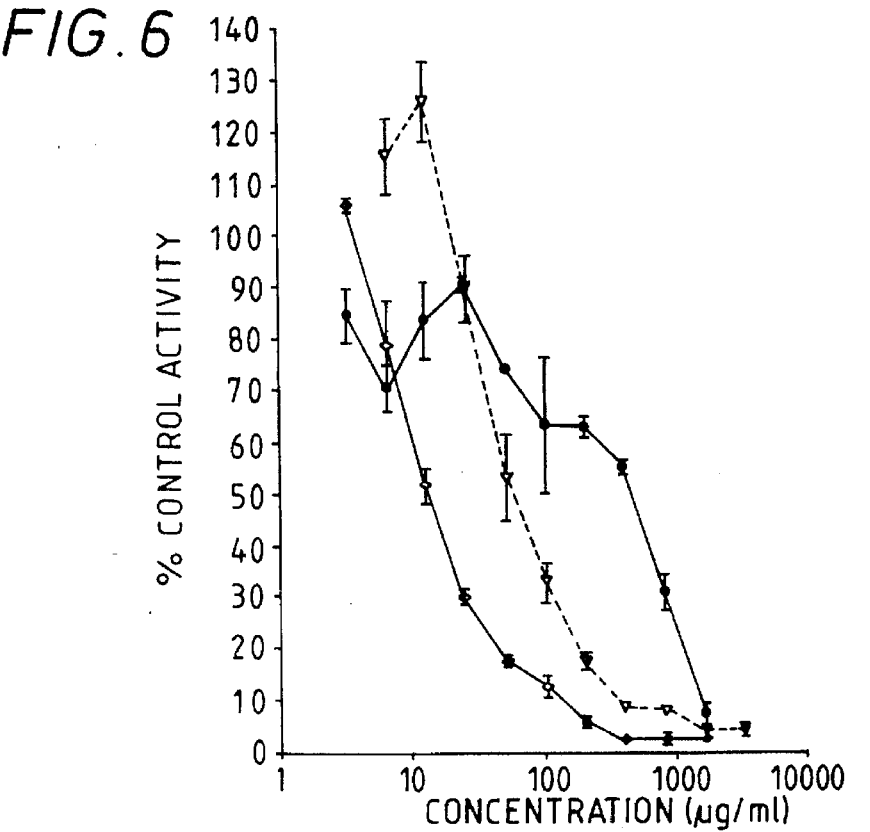
FIG. 6 shows a dose response curve for AZT vis 3TC.
Figure 7:
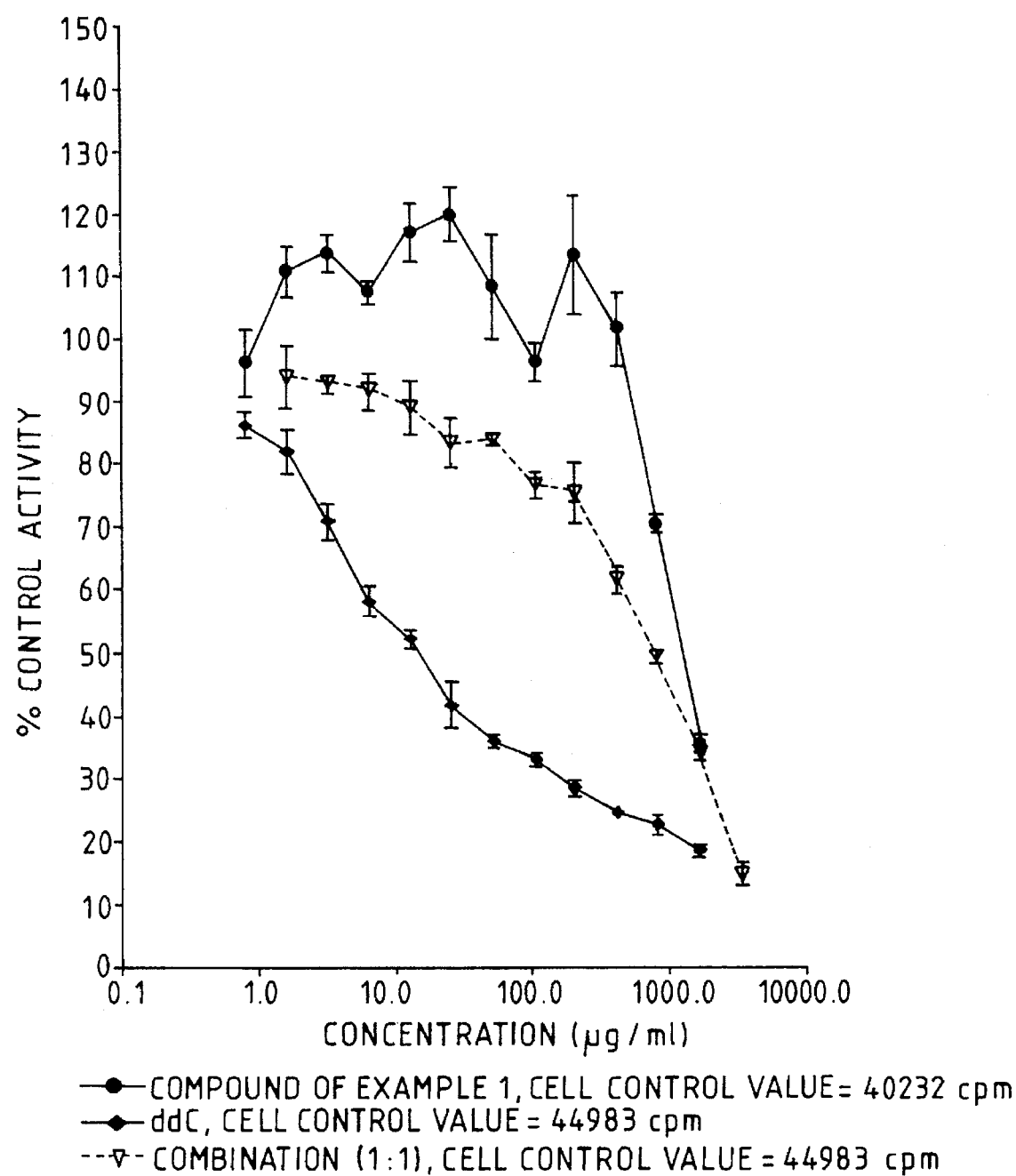
FIG. 7 shows a dose response curve for ddC vis 3TC.

Cytotoxicity was measured using a [$^3$H]-thymidine uptake assy. Dose-response curves obtained for AZT vis 3TC and ddC vis 3TC in a 1:1 combination in PBL cells are shown in FIGS. 6 and 7, respectively.

We claim:

1. A combination of drugs which are active against HIV wherein said combination comprises a mixture of first and second compounds wherein said first compound is (2R,cis)-4-amino-1-(2-hydroxymethyl-1,3-oxathiolan-5-yl)-1H-pyrimidin-2-one or a pharmaceutically acceptable salt, ester or salt of said ester of said first compound and said second compound is 3'-azido-3'-deoxythymidine or a pharmaceutically acceptable salt, ester or salt of said ester of said second compound; said first and second compounds being in a ratio which is synergistic against HIV wherein the ratio of said first compound to said second compound is from about 1.8:1 to about 167:1 by weight.

2. The combination of claim 1 wherein the mixture comprises (2R,cis)-4-amino-1-(2-hydroxy-methyl-1,3-oxathiolan-5-yl)-1H-pyrimidin-2-one and 3'-azido-3'-deoxythymidine.

3. A pharmaceutical formulation comprising a combination as claimed in claim 1 together with a pharmaceutically acceptable carrier therefor.

4. A method for the treatment of a mammal, including man, suffering from or susceptible to infection by HIV comprising administration of first and second compounds wherein first compound is (2R,cis)-4-amino-1-(2hydroxymethyl-1,3-oxathiolan-5-yl)-1H-pyrimidin-2-one or a pharmaceutically acceptable salt, ester or salt of said ester of said first compound and said second compound is 3'-azido-3'-deoxythymidine or a pharmaceutically acceptable salt, ester or salt of said ester of said second compound in a ratio of said first compound to said second compound which is about 1.8:1 to 167:1.

5. A method as claimed in claim 4 wherein said first and second compounds are administered sequentially.

6. A method as claimed in claim 4 wherein said first and second compounds are administered simultaneously.

* * * * *